United States Patent [19]

Goodey et al.

[11] Patent Number: 5,302,697
[45] Date of Patent: Apr. 12, 1994

[54] PEPTIDE AND DNA SEQUENCES

[75] Inventors: Andrew R. Goodey; Graham P. Belfield; Darrell Sleep, all of Nottingham, United Kingdom

[73] Assignee: Delta Biotechnology Limited, Nottingham, England

[21] Appl. No.: 67,243

[22] Filed: May 21, 1993

Related U.S. Application Data

[63] Continuation of Ser. No. 460,165, Mar. 13, 1990, abandoned.

[30] Foreign Application Priority Data

Jul. 23, 1988 [GB] United Kingdom ................ 8817598
Mar. 28, 1989 [GB] United Kingdom ................ 8906920

[51] Int. Cl.$^5$ .................... A61K 37/00; A61K 37/02; C07K 7/00; C12P 21/06
[52] U.S. Cl. ................................. 530/325; 530/326; 435/69.7
[58] Field of Search ................ 530/326, 325; 435/69.1

[56] References Cited

U.S. PATENT DOCUMENTS 4,588,684 5/1986 Brake ..................................... 435/68

FOREIGN PATENT DOCUMENTS 0123544 10/1984 European Pat. Off. .
0127304 12/1984 European Pat. Off. .
0206783 12/1986 European Pat. Off. .
0220689 5/1987 European Pat. Off. ...... C12N 15/00
0252561 1/1988 European Pat. Off. ...... C12N 15/00

OTHER PUBLICATIONS

Chemical Abstract, No. JP 63133986, Dialog Information Services. "DNA sequence coding secretory signal peptide—secretes protein when DNA sequence is integrated between promoter and exotic gene in yeast host".
Bathurst et al (1987) *Science* 235, 348–350.
Etcheverry et al (1966) *Bio/Technology* 4, 726–730.
Baldari et al (1987) *The EMBO J* 6, 229–234.
Stark et al (1986) *The EMBO J* 5(8), 1995–2002.
Tokunga et al (1987) *Biochem. Biophys. Res. Commun.* 144, 613–619.
Van Den Bergh et al (1987) *Eur. J. Biochem.* 144, 613–619.

*Primary Examiner*—Lester L. Lee
*Assistant Examiner*—A. M. Davenport
*Attorney, Agent, or Firm*—R. Hain Swope; Larry R. Cassett

[57] ABSTRACT

Secretory leader sequences, for use in secreting heterologous polypeptides in yeast, are formed by fusing part of the human serum albumin pre-sequence or part of the *Kluyveromyces lactis* killer toxin pre-sequence to the *Saccharomyces cerevisiae* mating factor alpha-1 KEX2 cleavage recognition site. The resulting fusion leader sequences are:

(a) $H_2N$-Met-Lys-Trp-Val-Ser-Phe-Ile-Ser-Leu-Leu-Phe-Leu-Phe-Ser-Ser-Ala-Tyr-Ser-Arg-Ser-Leu-Asp-Lys-Arg-COOH or (b) $H_2N$-Met-Asn-Ile-Phe-Tyr-Ile-Phe-Leu-Phe-Leu-Leu-Ser-Phe-Val-Gln-Gly-Ser-Leu-Asp-Lys-Arg-COOH

Conservative variations are also encompassed.

8 Claims, 6 Drawing Sheets

Plasmid pAYE 304

Fig. 5

Plasmid pAYE 305

Fig. 6

PEPTIDE AND DNA SEQUENCES

This is a continuation of application Ser. No. 07/460,165 filed Mar. 13, 1990 and now abandoned.

This invention relates to secretory leader sequences which can be employed to direct the secretion of a heterologous protein (such as human serum albumin) from fungi (for example the yeast *Saccharomyces cerevisiae*).

Translocation of protein molecules through bi-lipid membranes from one cellular compartment to another generally relies upon information held within the primary amino acid sequence of the protein itself. The most prevalent and therefore the best characterised sequence information is the amino terminal leader or signal sequence of prokaryotic and eukaryotic organisms. Genetic studies in which the signal sequence has been totally or extensively deleted indicate that the signal sequence is essential for protein translocation (Benson, S.A. et al. 1985, Ann. Rev. Biochem. 54, 101-134). Among several hundred known sequences (Watson, M. E. E., 1984, Nuc. Acid. Res. 12, 5145-5164) no consensus signal sequence or even an absolute requirement for any amino acid at any given position can be discerned, although a common feature of many leader sequences is a core of 7-10 hydrophobic amino acids. Genetic manipulations which result in alterations to the hydrophobic core, either by deletion or by inserting charged residues, generally result in a block in protein translocation (Benson, S. A., et al. 1985, Ann. Rev. Biochem. 54, 101-134). Moreover, in a series of extensive modifications to the chicken lysozyme leader sequence, Yamamoto et al. 1987 (Biochem. and Biophys. Res. Comm. 149, 431-436) have shown that, while some alterations to the hydrophobic core can result in the abolition of secretion, others can potentiate the leader sequence function, resulting in increased levels of protein secretion.

While the leader sequence is usually essential for the translocation of proteins across membranes, once translocated these sequences are usually endoproteolytically cleaved by enzymes contained within the cellular compartments into which the proteins have now moved. These enzymes recognise specific amino acid sequences within the primary structure of the translocated protein. Moreover, complete processing of certain eukaryotic proteins to their mature form often relies upon a series of proteolytic cleavages (Bussey, H., 1988 Yeast 4, 17-26).

With the recent advances in recombinant DNA technology, increasing resources have been brought to bear on the commercial exploitation of fungi, particularly yeasts, as vehicles for the production of a diverse range of proteins.

Since many of these proteins are themselves naturally secreted products, it is possible to utilise the information contained within the leader sequence to direct the protein through the secretion pathway. However, this information is contained within a peptide foreign to yeast. Its recognition and subsequent processing by the yeast secretory pathway are not necessarily as efficient as those of a homologous yeast leader sequence. As a consequence an alternative approach has been to replace the leader sequence with one derived from a naturally secreted yeast protein.

The most widely used yeast secretory sequence is the 89 amino acid leader sequence of the alpha-factor mating pheromone. Processing of this leader has been extensively studied (Kurjan & Herskowitz, Cell 30, 933-943, 1982; Julius et al. 1983 Cell 32, 839-852; Dmochowska et al. Cell 50, 573-584, 1987; Julius et al. Cell 36: 309-318, 1984; Julius et al. Cell 37, 1075-1085, 1984) and requires at least four gene products for complete proteolytic cleavage to liberate the mature 13 amino acid alpha-factor pheromone.

Complete proteolytic cleavage of the alpha-factor primary translation product requires first the removal of the N-terminal 19 amino acid signal sequence by a signal peptidase within the endoplasmic reticulum. Following this the sequential action of three gene products located within the golgi apparatus processes the large precursor molecule, liberating four copies of the alpha-factor pheromone. These are the KEX2 gene product, an endopeptidase which cleaves after the Lys-Arg dibasic amino acid pair, a carboxypeptidase $\beta$-like cleavage, recently identified as the product of the KEX1 gene, and a dipeptidyl amino peptidase, the product of the STE13 gene, which sequentially removes the Glu-Ala or Asp-Ala diamino acid pairing preceding the mature alpha-factor pheromone.

The alpha factor prepro leader sequence has successfully been employed to secrete a range of diverse proteins and peptides. However, when the alpha-factor signal is used to direct secretion of human serum albumin, we have found that a large proportion of the extracellular HSA produced is in the form of a 45 KD N-terminal fragment.

EP-A-252 561 (Sclavo) discloses the use of the 16 amino acid signal peptide (pre-sequence) from the killer toxin of *Kluyveromyces lactis* to aid secretion of heterologous proteins in yeast.

A further possibility is to use a fusion secretory leader sequence. This may be generated by the fusion of two independent sequences. A hybrid signal in which the first amino acids of the acid phosphatase signal were fused to the proteolytic cleavage site of human alpha interferon resulted in the expression and secretion of interferon (Hinnen et al. Foundation for Biochemical and Industrial Fermentation Research, 229, 1219-1224, 1983); 10% of the interferon produced was secreted into the medium. In a similar approach the first 22 amino acids of the alpha-factor leader were fused to the last twelve amino acids of the human interferon alpha-2 signal sequence resulting in the secretion of interferon alpha-2 into the culture supernatant (Piggott et al. Curr. Genet. 12 561-567, 1987). An identical construct in which the interferon alpha-2 gene was replaced by the interferon $\beta$ gene did not result in any secretion of human interferon $\beta$ into the culture supernatant. Finally, in a series of experiments designed to assess the effect of leader sequences on the secretion of human lysozyme, Yoshimura et al. (Biochem. & Biophys. Res. Comm. 145, 712-718, 1987) described a fusion leader comprising the first 9 amino acids of the chicken lysozyme leader and the last 9 amino acids of the *Aspergillus awamori* glycoamylase leader. Although this fusion leader was effective in secreting 60% of the produced material into the culture supernatant, it was only 15% as effective as the entire chicken lysozyme leader. Moreover, no secreted product could be detected if the human lysozyme sequences were preceded by the entire Aspergillus glycoamylase leader, or a fusion derived from the first 9 amino acids of the Aspergillus glucoamylase leader and the last 9 amino acids of the chicken lysozyme leader.

We have now devised new and advantageous leader sequences for use in fungi.

One aspect of the invention provides an amino acid sequence as follows:

(a) H₂N-Met-Lys-Trp-Val-Ser-Phe-Ile-Ser-Leu-Leu-Phe-Leu-Phe-Ser-Ser-Ala-Tyr-Ser-Arg-Ser-Leu-Asp-Lys-Arg-COOH or (b) H₂N-Met-Asn-Ile-Phe-Tyr-Ile-Phe-Leu-Phe-Leu-Leu-Ser-Phe-Val-Gln-Gly-Ser-Leu-Asp-Lys-Arg-COOH or conservatively modified variations of either sequence.

Table 1 shows alternative amino acids for each position except the initial methionine. Any of the possible permutations are within the scope of the invention. The selection of lysine or arginine for the last two positions is particularly non-critical, although there should always be Lys or Arg at each of these positions. Preferably, positions 20 and 21 of sequence (a) are not Gly and Val respectively. Sequences which are up to four amino acids shorter or longer are also included provided that the C-terminal (Lys, Arg), Lys-Lys or Arg-Arg entity is maintained, there is a positively charged residue within 5 residues of the N-terminus and there is a generally hydrophobic region at or adjacent the middle of the sequence.

forming growth factor β (Derynck et al (1985) Nature 316, 701-705), the 1-272 portion of Von Willebrand's Factor (Bontham et al, Nucl. Acids Res. 14 7125-7127), the Cathepsin D fragment of fibronectin (585-1578), α₁-antitrypsin, plasminogen activator inhibitors, factor VIII, α-globin, β-globin, myoglobin or nerve growth factor or a conservative variant of any of these. The polypeptide may also be a fusion of HSA or an N-terminal portion thereof and any other polypeptide, such as those listed above. Preferably, the polypeptide is a naturally-occurring human serum albumin, a modified human serum albumin or a fragment of either, such modified forms and fragments being termed "variants". These variants include all forms or fragments of HSA which fulfill at least one of the physiological functions of HSA and which are sufficiently similar to HSA, in terms of structure (particularly tertiary structure) as to be regarded by the skilled man as forms or fragments of HSA.

In particular variants or fragments of HSA which retain at least 50% of its ligand-binding properties, for example with respect to bilirubin or fatty acids, (preferably 80%, or 95%) are encompassed. Such properties are discussed in Brown, J. R. & Shockley, P. (1982) in Lipid-Protein Interactions 1, 26-68, Ed. Jost, P. C. & Griffith, O. H.

TABLE 1

Leader (a)

| 1 | | | | | | | | | 10 | | | | |
|---|---|---|---|---|---|---|---|---|---|---|---|---|---|
| Met | Lys | Trp | Val | Ser | Phe | Ile | Ser | Leu | Leu | Phe | Leu | Phe | Ser |
| | Arg | Phe | Leu | Thr | Trp | Leu | Thr | Ile | Ile | Trp | Ile | Trp | Thr |
| | His | Tyr | Ile | Gly | Tyr | Val | Gly | Val | Val | Tyr | Val | Tyr | Gly |
| | Gln | | Met | Ala | | Met | Ala | Met | Met | | Met | | Ala |
| | Asn | | | | | | | | | | | | |

| | | | | 20 | | | | | | 
|---|---|---|---|---|---|---|---|---|---|
| Ser | Ala | Tyr | Ser | Arg | Ser | Leu | Asp | Lys | Arg |
| Thr | Thr | Phe | Thr | Lys | Thr | Ile | Glu | Arg | Lys |
| Gly | Gly | Trp | Gly | His | Gly | Val | Asn | | |
| Ala | Ser | | Ala | Gln | Ala | Met | Gln | | |
| | | | | Asn | | | His | | |

Leader (b)

| Met | Asn | Ile | Phe | Tyr | Ile | Phe | Leu | Phe | Leu | Leu | Ser | Phe | Val |
|---|---|---|---|---|---|---|---|---|---|---|---|---|---|
| | Asp | Leu | Trp | Phe | Leu | Trp | Ile | Trp | Ile | Ile | Thr | Trp | Leu |
| | Glu | Val | Tyr | Trp | Val | Tyr | Val | Tyr | Val | Val | Gly | Tyr | Ile |
| | Gln | Met | | | Met | | Met | | Met | Met | Ala | | Met |
| | His | | | | | | | | | | | | |

| Gln | Gly | Ser | Leu | Asp | Lys | Arg |
|---|---|---|---|---|---|---|
| Asp | Ser | Thr | Ile | Asn | Arg | Lys |
| Asn | Thr | Gly | Val | Glu | | |
| Glu | Ala | Ala | Met | Gln | | |
| His | | | | His | | |

A second aspect provides a fusion compound comprising any of the said amino acid sequences linked, preferably directly, at the carboxyl terminal to the N-terminal residue of a polypeptide. The polypeptide may be any desired polypeptide, including "pro-polypeptides" (in other words precursors which undergo post-translational cleavage or other modification, such as glycosylation). The term "polypeptide" encompasses oligopeptides. The polypeptide may be fibronectin or a portion thereof (for example the collagen of fibrin-binding portions described in EP 207 751), urokinase, pro-urokinase, the 1-368 portion of CD4 (D. Smith et al (1987) Science 328, 1704-1707), platelet derived growth factor (Collins et al (1985) Nature 316, 748-750), trans- The portion of HSA disclosed in EP 322 094 is an example of a useful fragment of HSA which may be secreted by use of the leader sequences of the invention.

A third aspect provides a nucleotide sequence coding for any of the said amino acid sequences or for the said fusion compound. The nucleotide sequence (or the portion thereof encoding the leader sequence) may be selected from the possibilities shown in Tables 2 and 3, for sequences (a) and (b) respectively, where the codons encoding each amino acid are listed under the amino acids. The codons of Tables 2 and 3 clearly relate to RNA, but it is to be understood that equivalent DNA nucleotide sequences are also within the scope of this aspect of the invention.

TABLE 2

| Met | Lys | Trp | Val | Ser | Phe | Ile | Ser | Leu | Leu | Phe | Leu | Phe | Ser |
|---|---|---|---|---|---|---|---|---|---|---|---|---|---|
| AUG | AAA | UGG | GUU | UCU | UUU | AUU | UCU | UUA | UUA | UUU | UUA | UUU | UCU |

TABLE 2-continued

|  | AAG |  | GUC | UCC | UUC | AUC | UCC | UUG | UUG | UUC | UUG | UUC | UCC |
|---|---|---|---|---|---|---|---|---|---|---|---|---|---|
|  |  |  | GUA | UCA |  | AUA | UCA | CUU | CUU |  | CUU |  | UCA |
|  |  |  | GUG | UCG |  |  | UCG | CUC | CUC |  | CUC |  | UCG |
|  |  |  |  | AGU |  |  | AGU | CUA | CUA |  | CUA |  | AGU |
|  |  |  |  | AGC |  |  | AGC | CUG | CUG |  | CUG |  | AGC |
| Ser | Ala | Tyr | Ser | Arg | Ser | Leu | Asp | Lys | Arg |  |  |  |  |
| UCU | GCU | UAU | UCU | CGU | UCU | UUA | GAU | AAA | CGU |  |  |  |  |
| UCC | GCC | UAC | UCC | CGC | UCC | UUG | GAC | AAG | CGC |  |  |  |  |
| UCA | GCA |  | UCA | CGA | UCA | CUU |  |  | CGA |  |  |  |  |
| UCG | GCG |  | UCG | CGG | UCG | CUC |  |  | CGG |  |  |  |  |
| AGU |  |  | AGU | AGA | AGU | CUA |  |  | AGA |  |  |  |  |
| AGC |  |  | AGC | AGG | AGC | CUG |  |  | AGG |  |  |  |  |

TABLE 3

| Met | Asn | Ile | Phe | Tyr | Ile | Phe | Leu | Phe | Leu | Leu | Ser | Phe | Val |
|---|---|---|---|---|---|---|---|---|---|---|---|---|---|
| AUG | AAU | AUU | UUU | UAU | AUU | UUU | UUA | UUU | UUA | UUA | UCU | UUU | GUU |
|  | AAC | AUC | UUC | UAC | AUC | UUC | UUG | UUC | UUG | UUG | UCC | UUC | GUC |
|  |  | AUA |  |  | AUA |  | CUU |  | CUU | CUU | UCA |  | GUA |
|  |  |  |  |  |  |  | CUC |  | CUC | CUC | UCG |  | GUG |
|  |  |  |  |  |  |  | CUA |  | CUA | CUA | AGU |  |  |
|  |  |  |  |  |  |  | CUG |  | CUG | CUG | AGC |  |  |
| Gln | Gly | Ser | Leu | Asp | Lys | Arg |  |  |  |  |  |  |  |
| CAA | GGU | UCU | UUA | GAU | AAA | CGU |  |  |  |  |  |  |  |
| CAG | GGC | UCC | UUG | GAC | AAG | CGC |  |  |  |  |  |  |  |
|  | GGA | UCA | CUU |  |  | CGA |  |  |  |  |  |  |  |
|  | GGG | UCG | CUC |  |  | CGG |  |  |  |  |  |  |  |
|  |  | AGU | CUA |  |  | AGA |  |  |  |  |  |  |  |
|  |  | AGC | CUG |  |  | AGG |  |  |  |  |  |  |  |

A fourth aspect provides a DNA construct comprising a suitable control region or regions and a nucleotide sequence as defined above, the sequence being under the control of the control region. By "suitable control region" we mean such DNA regions as are necessary to enable the said nucleotide sequence to be expressed in the host for which the construct is intended. The control region will usually include transcriptional start and stop sequences, 3'-polyadenylation sequences, a promoter and, often, an upstream activation site for the promoter. The man skilled in the art will readily be able to select and assemble suitable regions from those available in this art. However, specific examples of suitable expression vectors and their construction include those disclosed in EP 198 745, GB 2 171 703 (for *B. subtilis*), EP 207 165, EP 116 201, EP 123 244, EP 123 544, EP 147 198, EP 201 239, EP 248 637, EP 251 744, EP 258 067, EP 268 424 and EP 322 094.

A fifth aspect provides a host transformed with the said DNA construct. The host may be any host in which the construct is found to work adequately, including bacteria, yeasts, filamentous fungi, insect cells, plant cells and animal cells. Preferably, however, the host is *Saccharomyces cerevisiae* or *Schizosaccharomyces pombe*, most preferably the former. As many native secretion signals are effective in heterologous hosts (for example the natural HSA leader sequence in yeast) it is entirely reasonable to suppose that the leader sequences of the invention will function in hosts other than yeasts.

A sixth aspect provides a process for preparing a polypeptide, comprising cultivating the said host and obtaining therefrom the polypeptide expressed by the said nucleotide sequence, or a modified version thereof. By "modified version thereof", we mean that the actual polypeptide which is separated may have been post-translationally modified, in particular by cleavage of the leader sequence.

A seventh aspect provides a polypeptide prepared by such a process.

So that the invention may be more readily understood, preferred aspects will now be illustrated by way of example and with reference to the accompanying drawings in which.

EXAMPLE OF A PRIOR ART TYPE OF LEADER SEQUENCE

The DNA coding sequence for mature HSA protein has been placed immediately downstream of a DNA sequence encoding the KEX2 cleavage site of the alpha factor pre pro leader sequence (85 amino acids). When this protein sequence is placed under the control of a promoter on a yeast autonomously replicating plasmid and transformed into a haploid strain of the yeast *Saccharomyces cerevisiae*, mature HSA can be detected in the culture supernatant. N-terminal amino acid sequence information indicates that the secreted protein has the same N-terminal amino acid composition as natural HSA, namely Asp-Ala-His. This also indicates that the first two amino acids of the secreted HSA are not susceptible to the dipeptidyl endopeptidase, the product of the STE13 gene, as this enzyme is responsible for the removal of such sequences from between successive repeats of the alpha-factor pheromone. Although mature HSA is the major product observed in the culture supernatant, a N-terminal fragment of HSA (45 kilodaltons) was also detected, representing approximately 15% of the total HSA synthesized. This fragment component represents not only a waste of secretion capacity but also certain downstream purification problems in that, as a fragment of HSA, it shares some biochemical and biophysical properties with intact HSA.

EXAMPLE 1

We have constructed a fusion leader which may be regarded as the natural HSA leader sequence from which the last five amino acids have been removed, to be replaced by the five amino acids preceding the KEX2 cleavage site of the alpha-factor pre pro leader sequence, i.e. amino acids 81 to 85 are Ser-Leu-Asp-Lys-Arg (Table 2).

When transformed with suitable plasmid vectors incorporating the fusion leader, yeast secrete mature HSA into the culture supernatant at levels comparable to that observed with the alpha-factor leader sequence. N-terminal sequence analysis indicates that the mature HSA possesses the correct N-terminal amino acid composition.

Moreover, substitution of the alpha-factor leader by the fusion leader sequence has been found to result in a 6 fold reduction in the levels of the 45 kd fragment observed in the culture supernatant. This therefore represents a significant improvement in the reduction of the contaminating polypeptides, thus aiding the purification of mature HSA from yeast culture supernatants.

Details

Figure 1:
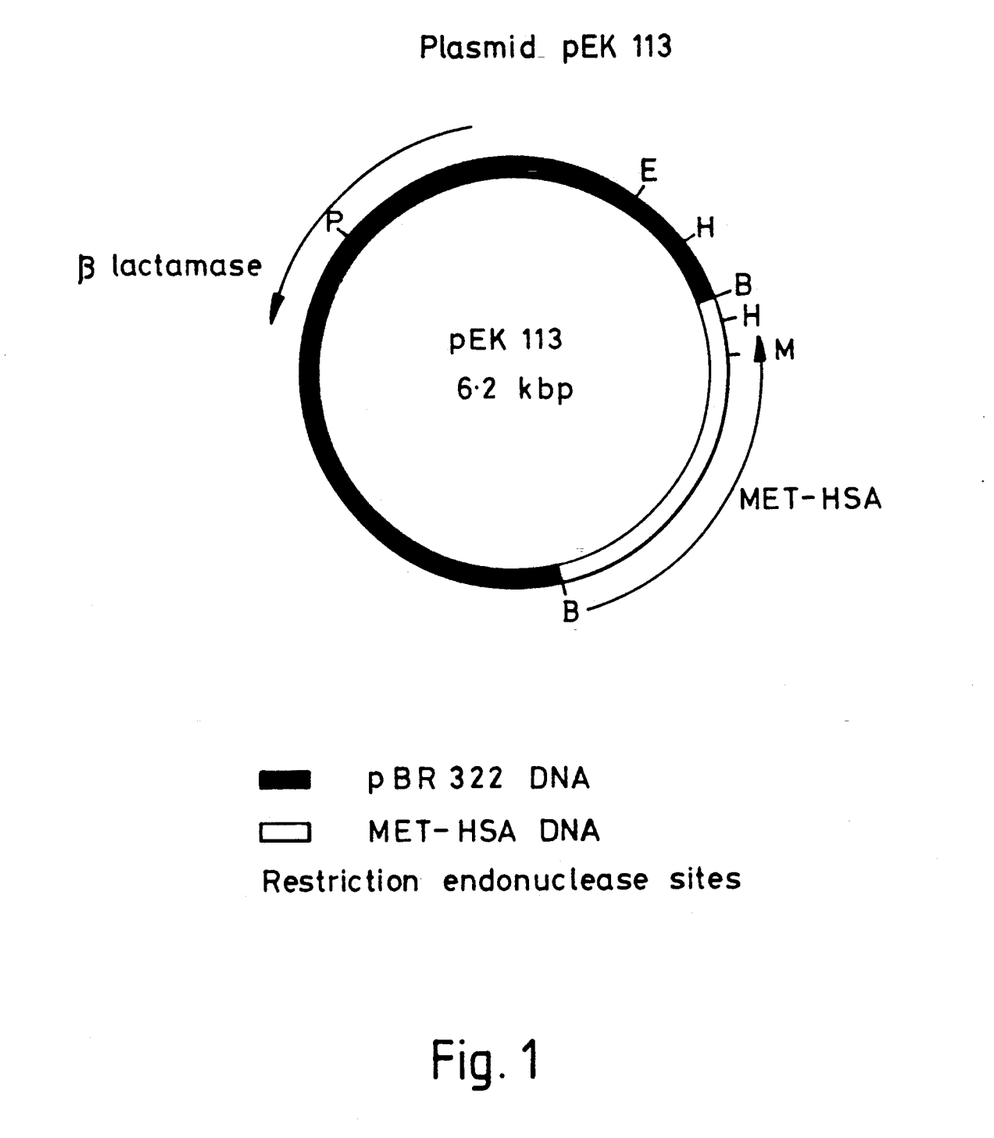
FIG. 1 is a restriction map of plasmid pEK113.

Unless otherwise stated all procedures were carried out as described by Maniatis et al (1982). Plasmid pEK113 (FIG. 1) (EP-A-248 637) was digested to completion with the restriction endonucleases MstII and HindIII. DNA was recovered by phenol/chloroform extraction and ethanol precipitation. The linearised plasmid DNA was then treated with the Klenow fragment of E. coli DNA polymerase I to generate a linearised DNA molecule with blunt ends.

The following oligonucleotide duplex (I) was constructed on an automated Applied Biosystems Inc 380B DNA synthesiser (according to manufacturer's instructions).

Oligonucleotide I
```
5'                                    3'
GGC TTA TAA GGA TCC TTA TAA GCC
CCG AAT ATT CCT AGG AAT ATT CGG
```

Figure 2:
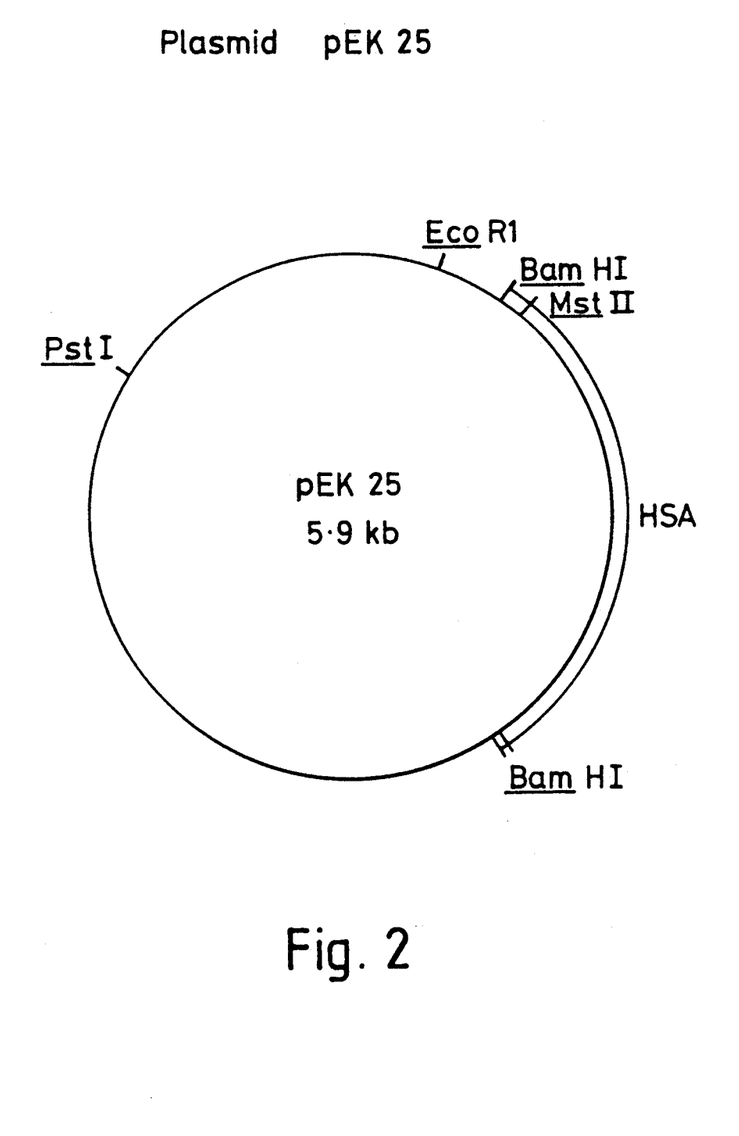
FIG. 2 is a restriction map of plasmid pEK25.

The oligonucleotide duplex was ligated with equimolar quantities of linearised, blunt ended pEK113. E. coli strain MC1061 was transformed with the ligation mixture and cells receiving DNA were selected on an ampicillin-containing medium (50 ug/ml ampicillin). Recombinant plasmids containing the oligonucleotide duplex were screened by digesting DNA prepared from individual colonies with the restriction endonucleases MstII and EcoRI. Plasmid pEK25 was thus formed (FIG. 2).

Plasmid pEK25 was digested to completion with the restriction endonucleases XbaI and BamHI, DNA fragments were separated by electrophoresis through a 1% (w/v) agarose gel and a 688 base pair XbaI-BamHi DNA fragment recovered from the gel by electroelution.

The plasmid mp19.7 (EP-A-248 637) was digested to completion with the restriction endonuclease XhoI. The linearised DNA was phenol/chloroform extracted and ethanol precipitated. The recovered DNA was then treated with the Klenow fragment of E. coli DNA polymerase I as previously described, following which the DNA was phenol/chloroform extracted and ethanol precipitated. The recovered DNA was then digested to completion with XbaI and the digestion products separated by agarose gel electrophoresis. A 1067 base pair fragment was recovered from the gel by electroelution. The following oligonucleotide duplex (II) was prepared as described previously.

Oligonucleotide II
```
5'
GATCC ATG AAG TGG GTA AGC TTT ATT TCC CTT CTT TTT CTC
      TAC TTC ACC CAT TCG AAA TAA AGG GAA GAA AAA GAG 3'
TTT AGC TCG GCT TAT TCC AGG AGC TTG GAT AAA AGA
AAA TCG AGC CGA ATA AGG TCC TCG AAC CTA TTT TCT
```

The plasmid pUC19 (Yanisch-Perron et al. 1985) was digested to completion with the restriction endonuclease BamHI. Linearised DNA was recovered by phenol/chloroform extraction and ethanol precipitation.

Figure 3:
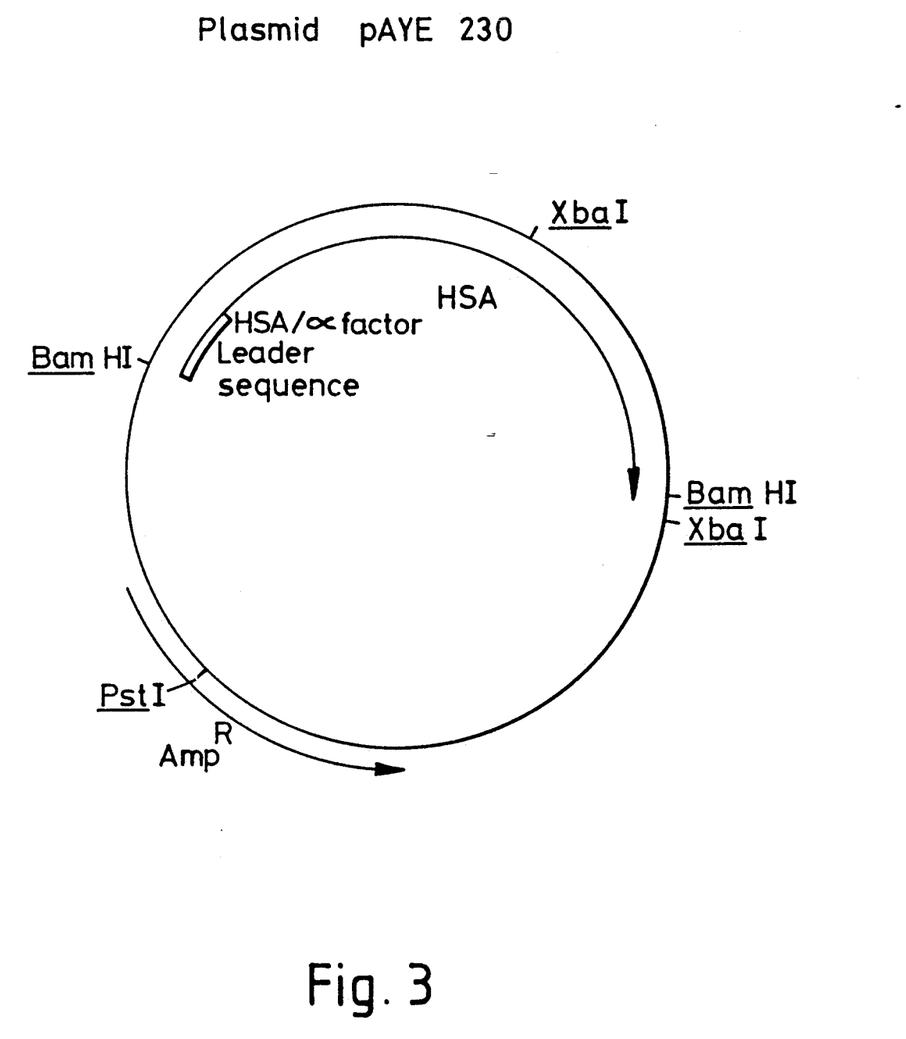
FIG. 3 is a restriction map of plasmid pAYE230.

Equimolar quantities of the BamHI digested pUC19, the oligonucleotide duplex II, the 1067 b.p. DNA fragment derived from mp19.7 and the 688 b.p. DNA fragment derived from pEK25 were ligated together. E. coli DH5 was transformed with the ligated DNA and transformants selected on 50 ug/ml ampicillin L-broth agar. Recombinant colonies containing the desired plasmid, designated pAYE 230 (FIG. 3) were selected by digested DNA obtained from individual colonies with the restriction endonuclease BamHI.

Plasmid pAYE 230 was digested to completion with BamHI and the products separated by electrophoresis through a 1% agarose gel. The 1832 base pair fragment containing the HSA coding sequence was recovered by electroelution.

Plasmid pMA91 (Mellor et al. 1983) was digested to completion with BglII under standard conditions. The linearised plasmid was phenol/chloroform extracted and ethanol precipitated.

Figure 4:
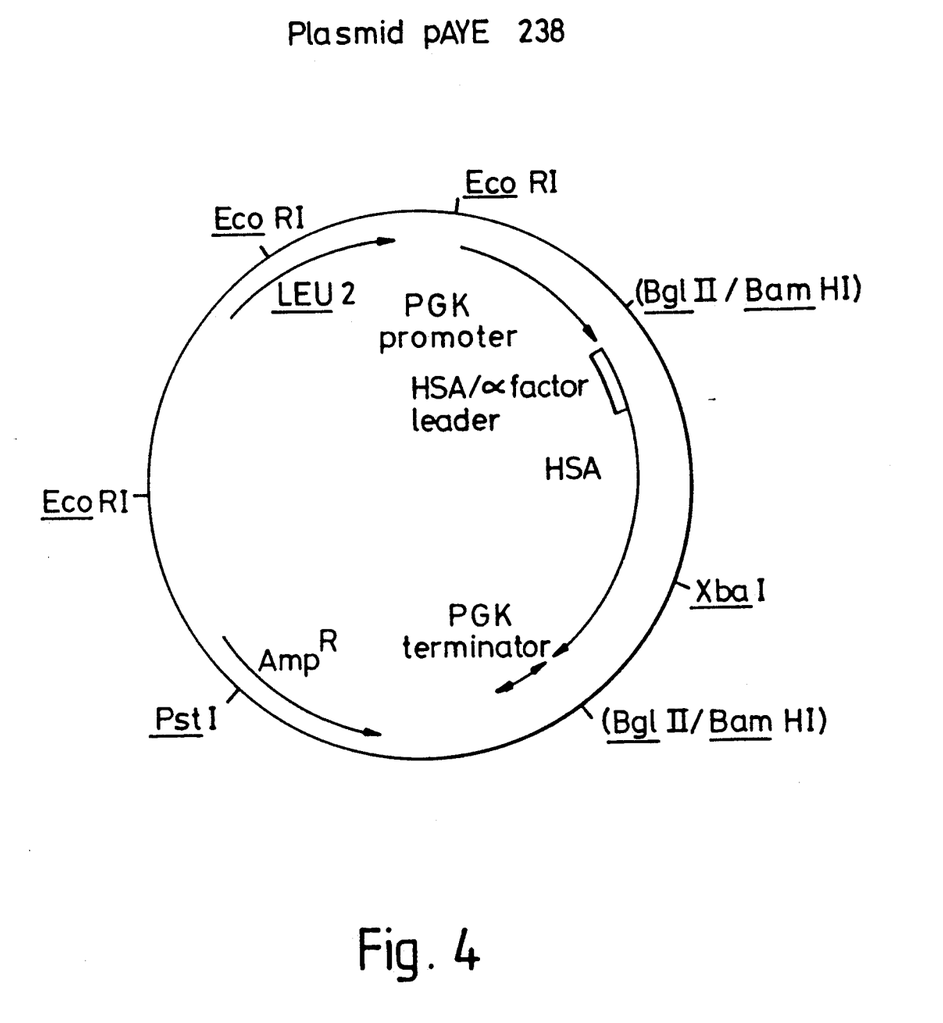
FIG. 4 is a restriction map of plasmid pAYE238.

Equivalent quantities of the linearised pMA91 and the DNA fragment prepared from pAYE 230 were ligated under standard conditions. E. coli DH5 was transformed with the ligation mixture and cells receiving the DNA selected on L-broth agar containing 50 μg/ml ampicillin. Colonies containing the desired plasmid, designating pAYE 238 (FIG. 4) were selected by digesting the DNA from such colonies with PvuII.

Plasmid pAYE 238 was transformed into the yeast Saccharomyces cerevisiae strain S150-2B as described by Hinnen et al. (1978). Cells receiving plasmid pAYE 238 were selected on minimal medium, supplemented with 2% (w/v) glucose, 20 mg/l histidine, 20 mg/l tryptophan and 20 mg/l uracil.

Transformed S150-2B cells were transferred to 10 ml YEPD media containing 2% (w/v) glucose and incubated at 30° C., 200 rpm for 72 hours. Cell free culture supernatants were analysed by discontinuous native 8-25% gradient polyacrylamide gel electrophoresis on a Pharmacia Phast System, as described in the manufacturer's instructions. Cells were stained and destained and the relative quantities of native HSA and HSA fragment estimated by gel scan at 595 nm.

EXAMPLE 2

We have also constructed a second fusion leader which consists of the 16 amino acid pre region of the 97,000 dalton *Kluyveromyces lactis* killer (ORF 2) toxin (Stark and Boyd, 1986, Tokumaga et al 1987) fused to the five amino acids preceding the KEX2 cleavage site of the alpha-factor prepro leader sequence, i.e. amino acids 81 to 85, Ser-Leu-Asp-Lys-Arg (Table 3).

When transformed with plasmid vectors incorporating the fusion leader described in Table 3, yeast secreted mature HSA into the culture supernatants at levels higher than when either the natural *K. lactis* prepro killer toxin leader sequence or the alpha-factor prepro leader sequence was used. N-terminal sequence analysis indicates that the mature HSA possesses the correct N-terminal amino acid composition.

Substitution of the alpha-factor leader by the *K. lactis* killer/alpha factor fusion leader sequence resulted in a six fold reduction in the levels of the 45 kd fragment observed in the culture supernatant. This therefore represents a significant improvement in the reduction of the contaminating polypeptides, thus aiding the purification of mature HSA from yeast culture supernatants.

Details

The experimental procedures employed to generate a yeast HSA secretion vector utilising the *K. lactis* killer/alpha factor fusion leader were identical to those described in Example 1, except that oligonucleotide duplex (II) was replaced by oligonucleotide duplex (III) synthesised on an automated Applied Biosystems Inc. 380B DNA synthesiser (according to manufacturer's instructions).

2% (w/v) glucose, 20 mg/l histidine, 20 mg/l tryptophan and 20 mg/l uracil.

Transformed S150-2B cells were transferred to 10 ml YEPD medium containing 2% (w/v) glucose and incubated at 30° C., 200 rpm for 72 hours. Cell free culture supernatants were analysed by discontinuous native 8-25% gradient polyacrylamide gel electrophoresis on a Pharmacia Phast System, as described in the manufacturer's instructions.

Cells were stained and destained and the relative quantities of native HSA and HSA fragment estimated by gel scan at 595 nm.

EXAMPLE 3

Using a vector based on the disintegration vectors of EP286424 (Delta Biotechnology), a suitable promoter and the fusion leader of Example 1 above, *Schizosaccharomyces pombe* (strain Leu1. 32 h) was transformed and fermented at 30° C. in 10 ml of EMM (Edinburgh minimal medium, Ogden, J. E. & Fantes, P.A. (1986) Curr. Genetics 10 509-514), buffered to pH 5.6 with 0.1M citric acid/sodium phosphate, to give 10-15 mg/l of HSA in the culture supernatant after 3 days.

REFERENCES

Beggs, J. D. (1978) Nature 275, 104-109.
Beggs, J. D. (1981), Molecular Genetics in Yeast, Alfred Benzon Symp. 16, 383-395.
Birnboim, H. C. & Doly, J. (1979) Nucl. Acids Res. 7,

| Oligonucleotide duplex III | | | | | | | | | | | | | |
| --- | --- | --- | --- | --- | --- | --- | --- | --- | --- | --- | --- | --- | --- |
| GATCC | ATG | AAT | ATA | TTT | TAC | ATA | TTT | TTG | TTT | TTG | CTG | TCA | TTC |
|  | TAC | TTA | TAT | AAA | ATG | TAT | AAA | AAC | AAA | AAC | GAC | AGT | AAG |
| GTT | CAA | GGA | AGC | TTG | GAT | AAA | AGA |  |  |  |  |  |  |
| CAA | GTT | CCT | TCG | AAC | CTA | TTT | TCT |  |  |  |  |  |  |

Figure 5:
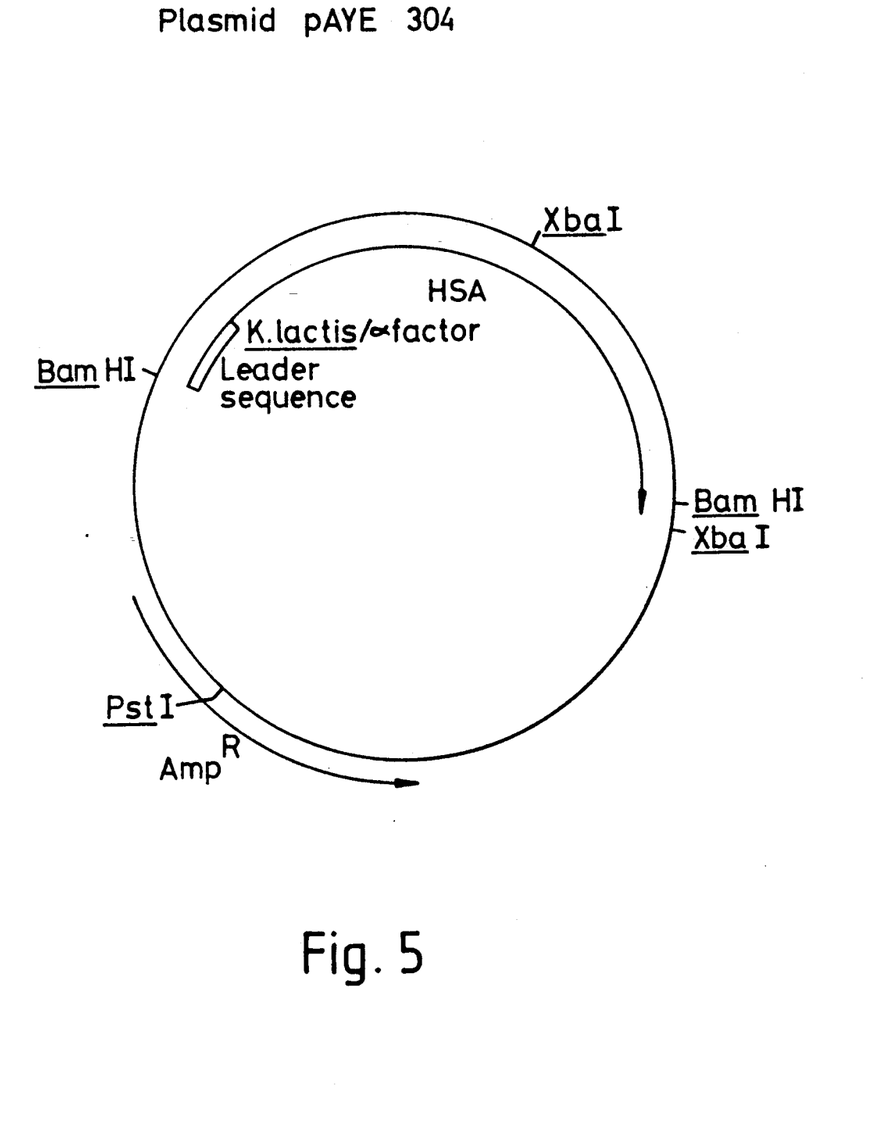
FIG. 5 is a restriction map of plasmid pAYE304.

Equimolar quantities of the BamHI digested pUC19, the oligonucleotide duplex III, the 1067 bp DNA fragment derived from mp 19.7 and the 688 b.p. DNA fragment derived from pEK25 were ligated together. *E. coli* DH5 was transformed with ligated DNA and transformants selected on 50 μg/ml ampicillin L-broth agar. Recombinant colonies containing the desired plasmid, designated pAYE304 (FIG. 5), were selected by digested DNA obtained from individual colonies with the restriction endonuclease BamHI.

Plasmid pAYE304 was digested to completion with BamHI and the products separated by electrophoresis through a 1% agarose gel. The 1823 base pair fragment containing the HSA coding sequence was recovered by electroelution.

Plasmid pMA91 (Mellor et al, 1983) was digested to completion with BglII under standard conditions. The linearised plasmid was phenol/chloroform extracted and ethanol precipitated.

Figure 6:
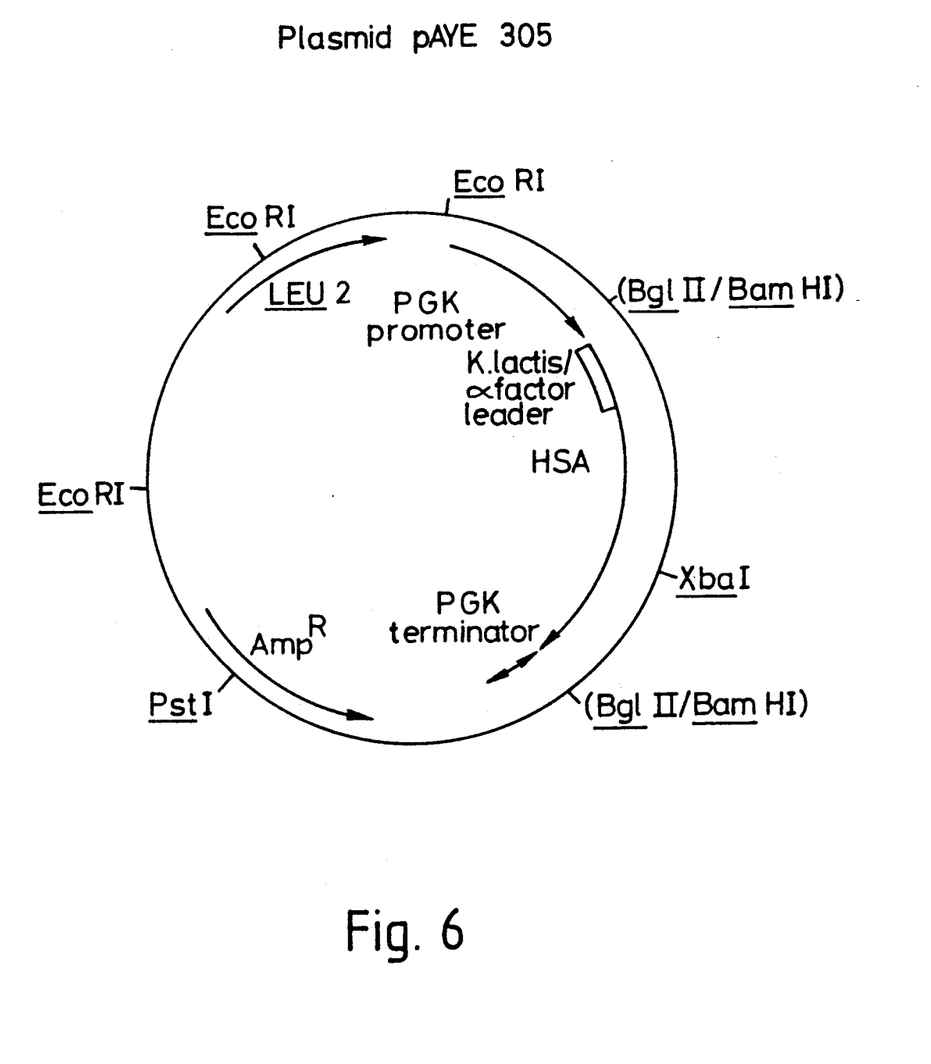
FIG. 6 is a restriction map of plasmid pAYE305.

Equivalent quantities of the linearised pMA91 and the DNA fragment prepared from pAYE304 were ligated under standard conditions. *E. coli* DH5 was transformed with the ligation mixture and cells receiving DNA selected on L-broth agar containing 50 μg/ml ampicillin. Colonies containing the desired plasmid, designating pAYE305 (FIG. 6), were selected by digesting the DNA from such colonies with PvuII.

Plasmid pAYE305 was transformed into the yeast *Saccharomyces cerevisiae* strain S150-2B as described by Hinnen et al, (1978). Cells receiving plasmid pAYE305 were selected on minimal medium, supplemented with 1513-1523.
Hanahan, D. (1983) J. Mol. Biol. 166, 557-580.
Henderson, R. C. A., Cox, B. S. & Tubb, R. (1985) Curr. Genet. 9, 135-136.
Hinnen et al. (1988) PNAS 75: 1929.
Hitzeman, R. A., Clarke, L. & Carbon, J. (1980) J. Biol. Chem., 255(24), 12073-12080.
Hitzeman, R. A., Hagie, F. E., Levine, H. L., Goeddel, D. V., Ammerer, G. & Hall, B. D. (1981) Nature 293, 717-722.
Julius, D., Brake, A., Blair, L., Kunisawa, R. & Thorner, J. (1984) Cell 37, 1075-1089.
Maniatis et al. (1982) Molecular Cloning: A Laboratory Manual, Cold Spring Harbor, N.Y.
Mandel, M. & Higa, A. (1970) J. Mol. Biol. 53, 159-162.
Mellor et al. (1983) Gene 24, 1-14.
Sherman, F., Fink, G. R. & Lawrence, C. (1979) Methods in Yeast Genetics, Cold Spring Harbor, N.Y.
Sleep, D., Belfield, G. P. & Goodey, A. R. (1988) Yeast 4 (14th Int. Conf. on Yeast Genet. & Mol. Biol., Helsinki, Conf. Poster).
Stark, M. J. R. & Boyd, A. (1986) E.M.B.O.J. 5, 1995-2002.
Tokumaga, M., Wada, N. & Hishinuma, F. (1987) Biochem. Biophys. Res. Comm. 144, 613-619.
Towbin, H., Staehelin, T. & Gordon, J. (1979). P.N.A.S. 76, 4350-4354.
Vogelstein, B. (1987), Anal. Biochem. 160, 115-118.
Yanisch-Perron et al. (1985) Gene 33 103-109.

We claim:

1. An amino acid sequence as follows:

(a) H₂N-Met-Lys-Trp-Val-Ser-Phe-Ile-Ser-Leu-Leu-Phe-Leu-Phe-Ser-Ser-Ala-Tyr-Ser-Arg-Ser-Leu-Asp-Lys-Arg-COOH; or (b) H₂N-Met-Asn-Ile-Phe-Tyr-Ile-Phe-Leu-Phe-Leu-Leu-Ser-Phe-Val-Gln-Gly-Ser-Leu-Asp-Lys-Arg-COOH; or a conservatively modified variant of either sequence, said sequence or variant being capable of providing for the secretion of a polypeptide fused thereto when the fused polypeptide is expressed in *S. cerevisiae*.

2. A non-naturally occurring fusion compound comprising an amino acid sequence according to claim 1 linked at the carboxyl terminal to the N-terminal residue of a polypeptide.

3. A non-naturally occurring fusion compound according to claim 2 wherein the said amino acid sequence is linked directly to said polypeptide.

4. A non-naturally occurring fusion compound according to claim 3 wherein the polypeptide is a naturally-occurring human serum albumin, a modified human serum albumin or a fragment of either.

5. A polypeptide obtained by a process comprising the following steps:

cultivating a fungal host transformed with a DNA construct, said construct including a suitable control region or regions, a nucleotide sequence coding for said polypeptide and a nucleotide sequence coding for the amino acid sequence of claim 1, said sequences being under the control of the control region, whereby said host expresses and secretes said polypeptide; and recovering said polypeptide.

6. A polypeptide obtained by a process comprising the following steps:

cultivating a fungal host transformed with a DNA construct, said construct including a suitable control region or regions, a nucleotide sequence coding for said polypeptide and a nucleotide sequence coding for the amino acid sequence of claim 1, said nucleotide sequence being selected from the sequences shown in Table 2 or 3, said sequences being under the control of the control region, whereby said host expresses and secretes said polypeptide; and recovering said polypeptide.

7. The polypeptide of claim 5 wherein said polypeptide is human serum albumin or a variant thereof.

8. The polypeptide of claim 6, wherein said polypeptide is human serum albumin or a variant thereof.

* * * * *